United States Patent [19]

Crowther et al.

[11] Patent Number: 5,116,728
[45] Date of Patent: May 26, 1992

[54] REAGENTS FOR $CO_2$ DETECTION

[75] Inventors: Fredric H. Crowther, Chadds Ford, Pa.; Wai T. Law, Sewell, N.J.

[73] Assignee: Em Diagnostic Systems, Incorporated, Gibbstown, N.J.

[21] Appl. No.: 554,512

[22] Filed: Jul. 20, 1990

[51] Int. Cl.$^5$ .................. C12Q 1/54; C12Q 1/58; C12Q 1/50; C12Q 1/26

[52] U.S. Cl. .................. 435/14; 435/17; 435/12; 435/25; 435/26; 436/8; 436/9; 436/18; 436/19

[58] Field of Search .................. 436/18, 125, 8, 9, 19; 435/174, 188, 4, 17, 14, 12, 25, 26; 424/94.1; 536/27

[56] References Cited

U.S. PATENT DOCUMENTS

| | | |
|---|---|---|
| 4,271,264 | 6/1981 | Modrovich ............ 435/17 |
| 4,277,562 | 7/1981 | Modrovich ............ 435/17 |
| 4,394,449 | 7/1983 | Modrovich ............ 435/17 |

OTHER PUBLICATIONS

Chenault et al., 1987, Review: Regeneration of Nicotinamide Cofactors for Use in Organic Synthesis Appl Biochem. Biotech. 14:147-197.
Tietz, ed., Textbook of Clinical Chemistry (W. B. Saunders Company: Philadelphia), pp. 1800-1801.
Wu et al., Clin. Chem. 32, 314-319 (1986).
Chenault et al., Appl Biochem. Biotech. 4, 147-197 (1987).
Morris et al., Clin. Chem. 36, 131-135 (1990).
Konopka et al., Clin. Chem. 36, 1068 (1990).

*Primary Examiner*—Christine Nucker
*Assistant Examiner*—David R. Preston
*Attorney, Agent, or Firm*—Millen, White & Zelano

[57] ABSTRACT

A stabilizer for maintaining a constant level of $CO_2$ in coenzyme containing enzymatic $CO_2$ diagnostic reagents is disclosed, comprising rate-limiting amounts of (a) the diagnostic reagents and (b) coenzyme-regenerating reagents, e.g., wherein (a) is malate dehydrogenase, phosphoenolpyruvate carboxylase and NADH, and (b) is glucose dehydrogenase and glucose, as are methods of use and kits containing a diagnostic reagent and stabilizer.

18 Claims, 3 Drawing Sheets

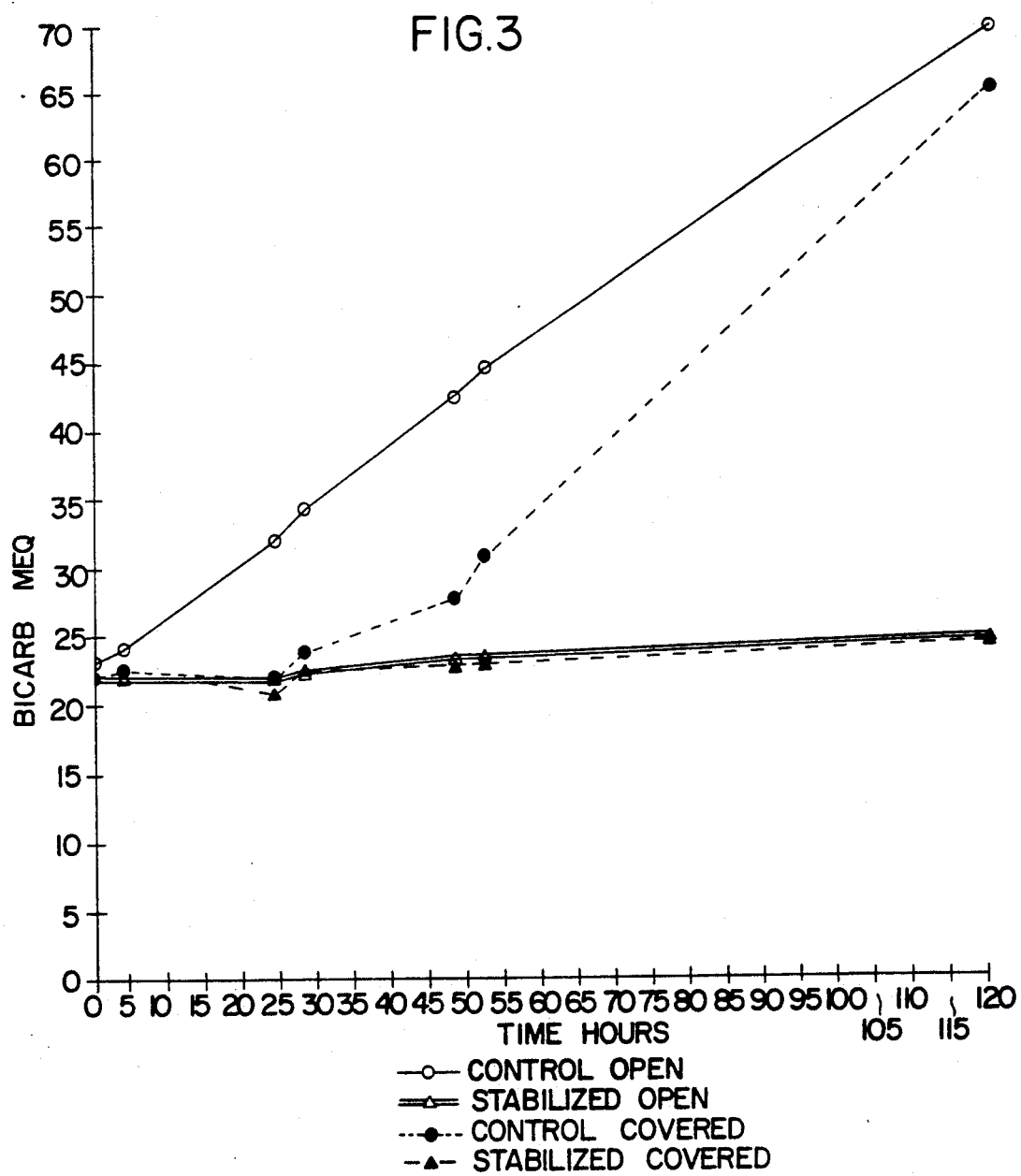

REAGENTS FOR CO2 DETECTION

BACKGROUND OF THE INVENTION

The present invention relates in general to enzymatic diagnostic reagents and methods of use, and in particular to stabilizers for coenzymes, especially for NADH- or NADPH-containing reagents for $CO_2$ detection.

The reduced forms of various compounds, e.g., nicotinamide adenine dinucleotide (NADH) and nicotinamide adenine dinucleotide phosphate (NADPH), are coenzymes, as the hydrogen donors, for reactions catalyzed by many enzymes, e.g., dehydrogenases. Similarly, the oxidized forms of coenzymes are hydrogen acceptors for other enzymatic reactions. These enzymatic reactions requiring coenzymes have a wide variety of uses in pharmacology, chemical syntheses, and clinical diagnostics.

In particular, reactions which either consume or produce NADH or NADPH are easily detectible by measuring the UV absorbance of solutions containing them at about 340 nm, the absorption maximum of NADH and NADPH. These reactions can be used to directly measure the presence of an analyte in the solution. For example, the presence of a substance which is either a substrate for, or an enzyme which is a catalyst for, a particular reaction can be detected by adding it to a diagnostic agent comprising either the enzyme for the reaction, or the substrate for the reaction, respectively, in the presence of a given amount of a coenzyme required for the reaction, and measuring the appearance or disappearance of the reduced or oxidized form of the coenzyme.

Alternatively, a first enzyme reaction which is to be detected, but which does not produce or consume detectable reagents, may be indirectly coupled to a second reaction which does produce detectable products, by having in the diagnostic reagent a second enzyme/coenzyme combination which can be used to detect the appearance or disappearance of a substrate for the second enzyme which is produced or consumed during the reaction of the first enzyme upon it. Thus, for example, in order to measure the presence of the very important enzyme SGOT (serum glutamic-oxaloacetic transaminase, which enzyme is released into the blood after a myocardial infarct), the diagnostic agent contains aspartate and α-ketoglutarate, which are converted by SGOT to glutamate and oxaloacetate.

This indirect method of measurement thus allows detection of analytes which are not themselves either substrates or enzymes involved in NADH production or consumption.

However, a major and thus-far unsatisfactorily-resolved problem in this field is that the coenzymes for these reactions, in addition to being oxidized, e.g., to $NAD^+$ and $NADP^+$, respectively, during the reactions proper, are very susceptible to undesired oxidation, by, e.g., dissolved oxygen, as well as to decomposition of the oxidized form, prior to use, both when the compounds are in dry form and when they are in solution. In particular, NADH and NADPH are known to be unstable in solution, especially under acidic conditions (Wu et al., Clin. Chem. 32, 314-319 (1986); Lowry et al., J. Biol. Chem. 236, 2756-2759 (1961); Burton et al., Arch. Biochem. Biophys. 101, 150-159 (1963)).

The stability of these coenzymes in diagnostic reagents is of particular importance, as is evident by the many attempts in the prior art to stabilize them, again, both in dry powder form as well as in solution. These previous attempts have included stabilizing the coenzyme test composition using sulfhydryl-containing compounds (U.S. Pat. No. 3,746,625), other special stabilizers (Chem. Abstr. Vol. 104, No. 11, Sec. 109, Abstr. No. 084922), or preserving the coenzymes in an organic solvent matrix (U.S. Pat. No. 4,277,562). The most successful approach has been to maintain the coenzymes at an alkaline pH (e.g., at a pH >8.0) with a suitable buffer (Wu, supra). However, no effective method has been suggested to maintain a stable NADH or NADPH solution at a pH below 8.0, especially in buffers that have a high concentration of phosphate anion (Wu, supra).

It is also acknowledged that the reductive regeneration of NADH and NADPH via enzymatic, chemical or other physical methods is well known in organic syntheses and bioreactors in order to decrease the cost incurred by continually adding large amounts of the expensive reduced coenzymes (Chenault et al., Appl. Biochem. Biotech. 4, 147-197 (1987); Wong et al., J. Am. Chem. Soc. 103, 4890-4899 (1981); Wong et al., Am. Chem. Soc. 107, 4028-4031 (1985); Suye et al., Enz. Microb. Technol. 7, 418-424 (1985); U.S. Pat. No. 4,766,071; Wang et al., Biochem. Eng. 12 119-146 (1979)). However, such regeneration would have been expected to be detrimental to the stabilizing of diagnostic reagents which utilize coenzymes which depend

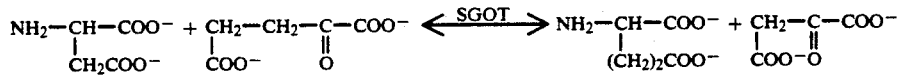

However, none of these compounds is easily detectable spectrophometrically, or by other simple methods. Therefore, in order to detect this first reaction, it is coupled to another reaction in which the thus-formed oxaloacetate is converted to malate by a second enzyme, malate dehydrogenase, with the concomitant oxidation of NADH into $NAD^+$, this second reaction being detectable spectrophotometrically by the disappearance of NADH:

upon the quantitative determination of NADH as a means of detection. This is because when the production or disappearance of the coenzyme is used to measure the concentration of the diagnostically significant analyte, the addition of $NAD^+$-reducing enzymes would be expected to seriously distort the results of those diagnostic tests, by changing the levels of the very reactant which is to be measured.

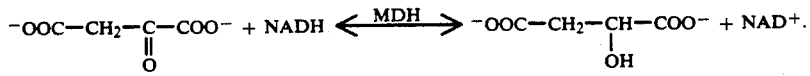

SUMMARY OF THE INVENTION

One aspect of the present invention is to provide a method of stabilizing a reduced form of a coenzyme in a solution containing a diagnostic reagent for $CO_2$ detection which requires a coenzyme for activity, said coenzyme capable of existing in a reduced or oxidized form, wherein the diagnostic reagent comprises a first and a second diagnostic enzyme, which are phosphoenolpyruvate carboxylase and malate dehydrogenase, respectively, and a diagnostic substrate, which is phosphoenolpyruvate, and detects the presence and amount of $CO_2$ in a sample by measuring the oxidation of reduced coenzyme caused by an enzymatic diagnostic reaction for which $CO_2$ is a substrate, said oxidation occurring at a rate proportional to the amount of $CO_2$ in the sample, comprising adding to said diagnostic reagent a stabilizer, wherein said stabilizer comprises (a) a stabilizer enzyme which reduces the oxidized form of the coenzyme; and (b) a substrate for the stabilizer enzyme; wherein the amount of (a) or (b) in the solution is rate-limiting and sufficiently low to reduce the oxidized coenzyme at a rate which is less than 10% of the lowest expected diagnostically significant rate of oxidation of the diagnostic reaction, and wherein said stabilizer further comprises a rate-limiting and thereby $CO_2$-stabilizing amount of one of said first or second diagnostic enzymes and a non-rate-limiting amount of the other of said diagnostic enzymes, and wherein said rate-limiting amount of one of the first or second diagnostic enzyme is sufficiently low to remove dissolved $CO_2$ from the solution at a rate which is less than 10% of the lowest expected diagnostically significant rate of removal of $CO_2$ of the diagnostic reaction. In a preferred embodiment, the amount of (a) or (b) is effective to achieve a substantially constant amount of reduced coenzyme in the solution under storage conditions.

A second aspect of this invention provides a stabilized diagnostic reduced coenzyme-requiring enzymatic reagent for $CO_2$ which is a substrate for a diagnostic enzyme, comprising:

(a) the diagnostic enzyme, (b) a reduced coenzyme for said diagnostic enzyme, (c) a stabilizing enzyme which reduces the coenzyme, (d) a stabilizing substrate for the stabilizing enzyme;

(e) a rate-limiting and thereby $CO_2$-stabilizing amount of one of said first or second diagnostic enzymes; and (f) a non-rate-limiting amount of the other of said diagnostic enzymes; and wherein the amount of (c) or (d) in the solution is sufficiently low to reduce the oxidized coenzyme at a rate which is less than 10% of the lowest expected diagnostically significant rate of oxidation of the diagnostic reaction, and wherein said rate-limiting amount of one of the first or second diagnostic enzyme is sufficiently low to remove dissolved $CO_2$ from the solution at a rate which is less than 10% of the lowest expected diagnostically significant rate of removal of $CO_2$ of the diagnostic reaction. In a preferred embodiment, the amount of (c) or (d) is effective to achieve a substantially constant level of oxidized or reduced coenzyme in the solution under storage conditions. Preferably, the stabilizer also includes an amount of (g) an oxidized coenzyme sufficient to establish equilibrium conditions at a particular concentration of reduced coenzyme.

In a further preferred embodiment, the amount of the first or second diagnostic enzyme is effective to achieve a substantially constant amount of dissolved $CO_2$ in said first compartment under storage conditions.

A third aspect of this invention is a kit containing a stabilized reagent for $CO_2$ determination as described above, wherein said reagent is present in at least two separate components, a first component (i) containing said diagnostic substrate for the first diagnostic enzyme, reduced coenzyme for said second diagnostic enzyme, buffer, and said stabilizer, and a second component (ii) containing diagnostically effective amounts of said first and second enzymes.

Upon further study of the specification and appended claims, further objects and advantages of this invention will become apparent to those skilled in the art.

Various other objects, features and attendant advantages of the present invention will be more fully appreciated as the same becomes better understood when considered in conjunction with the accompanying drawings, and wherein:

FIG. 3 shows the effect of adding the $CO_2$ stabilizer of this invention to an enzymatic $CO_2$ assay as compared with the stability of the unstabilized $CO_2$ assay.

Figure 1:
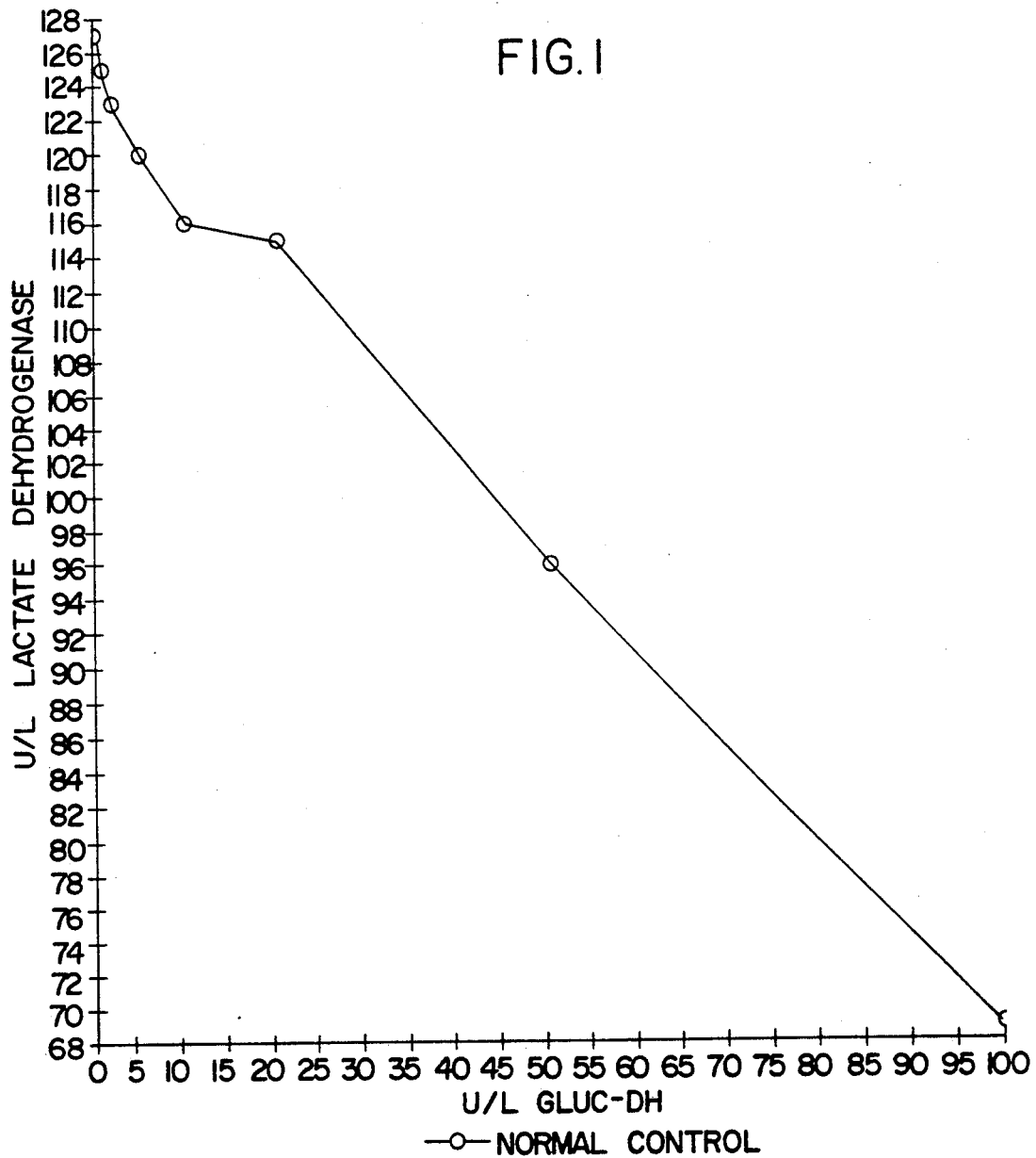
FIG. 1 shows the interference of glucose dehydrogenase (GDH) in the lactate dehydrogenase (LDH) assay; the graph shows that as GDH increases, the amount of LDH detected decreases.

It has been thus discovered that a coenzyme stabilizer according to this invention can function in conjunction with diagnostic reagents which utilize these coenzymes if careful control is achieved over the rate of reduction of the reduced form, such that an equilibrium is maintained at a particular ratio of the concentration of reduced to oxidized form, for example, the ratio of [NADH]/[NAD+]. Such control can be achieved if the reaction catalyzed by the stabilizer is slow and controllable, and preferably stops at a predicted equilibrium. The term "slow" as used herein means occurring at a rate which is a small fraction, e.g., less than 10%, preferably less than 5% and most preferably less than 2%, of the diagnostically significant rate of reaction of the diagnostic assay. By "diagnostically significant rate of reaction" is meant the rate of reaction which is required to determine the smallest or largest reasonably expected amount of analyte in a potential sample. Thus, for example, if the smallest amount of analyte to be detected in a given assay results in a disappearance of NADH of 10 $\mu$M/min (after 1:10 dilution, typical of a sample:reagent dilution, therefore, adding 1 $\mu$M/min overall), a suitable amount of stabilizer enzyme would provide a rate of reaction reducing NADH of 0.1 $\mu$M/min, preferably 0.02 $\mu$M/min or less.

This equilibrium is effected by employing a stabilizer, e.g., an enzyme in conjunction with a substrate therefor, which can reduce oxidized NAD+ or NADP+ at a controlled rate. This controlled rate is preferably such that a substantially constant level of the desired reactant, e.g., NADH, is maintained during storage. By "substantially constant" is meant not increasing or decreasing more than 10%, preferably less than 5% and most preferably less than 2%, during the relevant storage period. However, stabilization of the diagnostic assays according to the present invention also includes slowing the rate of NADH oxidation to less than 50%, and preferably less than 10%, of the rate of oxidation for unstabilized assays. Thus, contrary to the previous NADH-regenerating protocols reported in the literature, it is undesirable for the purposes of this invention to achieve a maximum speed of regeneration of the one form from the other, e.g., NADH from NAD+. Instead, it was necessary to conceive a means for achieving the recovery of the desired form at a slow and controlled rate.

The desired result of providing a diagnostically-useful coenzyme stabilizer has been achieved by the stabilizer according to the present invention, by utilizing carefully selected catalysts and other workable conditions. In the case where the catalyst is an enzyme which can perform the required reduction, these conditions generally include a very high stabilizer substrate concentration, a defined concentration of coenzyme in the undesired state, e.g., NAD+, and a very low amount of stabilizer enzyme. By "a very high substrate concentration" is meant in vast excess of the amount of substrate required to drive the reaction in the desired direction, i.e., towards NADH-recovery, and sufficient to provide a continuing source of a suitable excess over the usable time period in which the diagnostic assay is to be stabilized. By "a very low amount of stabilizer enzyme" is meant an amount which is rate-limiting for the reaction, and which is sufficiently low that it provides, in the presence of an excess of stabilizer substrate and sufficient NAD+, a rate of reaction less than about 10%, preferably less than 2%, of the diagnostically significant rate of reaction for the assay reagent which is being stabilized. By "rate-limiting" is meant that the concentration of the thus-described component of the reaction is such that, if more were added, the entire reaction would go faster, as there is a sufficient amount of the remainder of the components of the reaction to allow a faster reaction.

Thus, it can be seen that there is a vast difference between this invention and the prior art methods of regenerating NADH. In the prior art, the purpose of the NADH regeneration is to provide a relatively unlimited supply of the coenzyme for the primary reaction of interest throughout the course of that reaction by means of coupling that first reaction to a second reaction which causes the regeneration of the reduced NADH at a rate of reaction at least as high as the primary diagnostic oxidation reaction of the NADH. Clearly, this method of regeneration of NADH would render useless the diagnostic reagents of the instant invention, which depend upon the quantitative determination of NADH as a means of detection of the presence of analytes in a sample. If the NADH were being regenerated at any appreciable rate, e.g., as fast as it was being oxidized in the diagnostic reaction or at any significant percentage of that rate, e.g., greater that 10%, the assay would be useless for detecting the presence of any analyte. Thus one of ordinary skill in the art of enzymatic diagnostic tests would not expect that regeneration of NADH would be a suitable way to stabilize NADH in NADH-containing diagnostic reagents which depend upon detection of NADH for the measurement of the presence of analyte.

However, it has been unexpectedly found that when equilibrium conditions are determined for the amount of NADH present in a particular diagnostic reagent, as balanced against the expected rate of oxidation of the NADH under a particular set of conditions, e.g., storage conditions, a stabilizing amount of an NAD+-reducing stabilizer, e.g., a catalyst, e.g., an enzyme and substrate therefore, can be determined which, when added to a diagnostic reagent which depends upon detection of NADH for the measurement of the presence of analyte, provides a suitable rate of recovery of the oxidized NAD+, yet does not catalyze the reaction at a rate fast enough to interfere with the primary diagnostic reaction of interest, once said diagnostic reaction is initiated by the addition of the analyte or other missing reactant.

Thus, the term "regeneration" as applied to the reaction of NAD+ being reduced to NADH, an used herein, refers to the conventional reaction at the highest possible rate which has been used in the prior art to regenerate NADH used up during the course of a hydrogen atom donor-requiring primary reaction. This term is to be contrasted with the term "recovery" as applied to the reoxidation of NAD+ to NADH at a controlled rate, i.e., at a rate which is a fraction of the diagnostically significant rate for the primary diagnostic reaction, under equilibrium conditions, as used herein.

In the case when the catalyst is an enzyme, the following conditions are preferred:
(a) The stabilizing enzyme must itself be stable;
(b) Any additional substrates and cofactors needed for the reaction must also be stable; and
(c) The reaction catalyzed by the stabilizing enzyme must be slow and controllable, and, ideally, should stop at a predicted equilibrium.

Thus stabilizers of this invention include any enzyme and appropriate substrate therefor which are involved in the catalysis of a reaction wherein NAD+ is reduced, including, inter alia, the following enzyme/substrate pairs:

| ENZYME | SUBSTRATE |
|---|---|
| Glucose Dehydrogenase (GDH) | glucose |
| Lactate Dehydrogenase (LDH) | lactate |
| Sorbitol Dehydrogenase | sorbitol |
| Galactose Dehydrogenase | galactose |
| Alcohol Dehydrogenase | ethanol |
| Glucose-6-Phosphate Dehydrogenase | glucose-6-phosphate |
| Glutamate Dehydrogenase | glutamate |
| Glycerol Dehydrogenase | glycerol |

In particular, it is noted that dehydrogenases are generally suitable. Suitable enzymes include those available commercially, as well as any other enzyme suitable for diagnostic purposes and which utilize a coenzyme for which stabilization according to this invention would be useful.

The choice of substrate and any other required cofactors for the reaction will vary depending upon which stabilizing enzyme is selected, but will be well known to those of ordinary skill in enzyme technology. For example, for the glucose dehydrogenase stabilizer, glucose is the substrate for the reaction which co-generates NADH from NAD+.

Suitable coenzymes for this stabilization reaction include NADH and NADPH in their reduced or oxidized forms, as appropriate, as well as any derivatives thereof which will function in conjunction with a stabilizing enzyme or catalyst, for example, thio-NADH (Dolan, P.A., Clin. Chem. 35, 1858 (1989).

The determination of appropriate concentrations of the various components of the stabilizer will vary according to which enzyme is being used, the nature of the material to be stabilized, the temperature at which it is to be stored, etc. However, for any particular set of conditions, these concentrations can be routinely determined according to the principle discussed above by those of ordinary skill in enzyme technology following various routine optimization protocols.

In addition, there are the following guidelines for the determination of the concentrations of the reactants:

1. The maximum amount of NADH which can be present in the diagnostic reagent in final form is limited by the sensitivity of the spectrophotometer at the measuring wavelength; in general, the limits of the current technology are such that the absorbance should be less than 3.0 A (absorbance units), e.g., a concentration of NADH of 0.47 mM at 340 nm will have an absorbance of about 3.0. At higher concentrations, the relationship between concentration of NADH and absorption at 340 nm is no longer linear, and it is therefore not relevant to diagnostic considerations. A similar calculation can be made for NADH at other wavelengths and corresponding molar absorptivities.

2. Suitable concentrations for the catalyst for the recovery reaction are easily determinable. If the catalyst is to be the rate-limiting reactant, in each case what is determined is the concentration of catalyst which will catalyze the reaction at a rate which approximates the rate of oxidation of the NADH under the pertinent storage conditions, and that rate is balanced against the rate of reaction of the diagnostic reaction of interest, which must be high enough to substantially overwhelm the rate of the NADH recovery reaction in the time frame of the diagnostic determination.

3. In general, it will be most expedient if the catalyst is the rate-limiting component in the stabilizer. However, it can be envisioned under some circumstances that the substrate could be rate-limiting rather than the catalyst. Suitable concentrations of substrate are similarly readily determinable by one of ordinary skill in the art.

In order to determine suitable conditions, e.g., concentrations of enzymes, coenzymes, buffers, etc., only routine experimentation fully conventional to one of ordinary skill in the art is required, once the desired result is understood. Thus, preferred concentrations of the standard diagnostic reagents will be generally the same as in the assays used conventionally, and amounts of stabilizing reagents can be routinely determined. In particular, using standard analytical techniques well known to one of ordinary skill in the art, calculations and routine experiments can be performed which will enable a person so skilled to determine suitable concentrations of the various diagnostic components and stabilizer components.

In particular, in order to maintain the usefulness of the diagnostic reagent, the recovery reaction must proceed at a rate which is compatible with the rate of the diagnostic reaction under assay conditions. Thus it is preferred that the recovery reaction proceed at a rate which is less than 10% preferably less than 5% and most preferably less than 2% of the rate of the diagnostic reaction in order to minimize interference of the recovery reaction with the diagnostic reaction. For example, in a standard glutamate-pyruvate transaminase (GPT) assay at 37° C., 25 U/L of analyte enzyme is a normal concentration, units being a measure of enzyme in terms of the rate of reaction in a given amount of time. In order to achieve less than a 2% interference by the recovery reaction, the amount of stabilizer present should provide a recovery reaction corresponding to a rate provided by 0.5 U/L. Since, as noted above, it has been found to be preferable to limit the amount of enzyme rather than the amount of substrate in order to control the rate of reaction, an amount of stabilizer enzyme is chosen that provides that rate of recovery reaction, while providing excess of the stabilizer substrate.

In the exemplary case of the GPT diagnostic reagent, a suitable stabilizer enzyme is GDH and the stabilizer substrate is glucose, which is provided in excess, e.g., a 100-fold excess. Since the standard conditions for the GPT diagnostic reaction include 0.27 mM NADH, the equilibrium reaction for the GDH should be set up such that $$K = \frac{[\text{gluconolactone}][NADH]}{[\text{glucose}][NAD^+]}.$$

In order to determine the appropriate concentrations of these substrates, it is necessary to determine the equilibrium conditions for the enzyme under suitable conditions. In this case, for GDH at a concentration of 1 U/L, it was found that the equilibrium ratio of NADH/NAD+ is about 6.1. It was further found that the recovery reaction can be stopped at a predetermined level of NADH according to the level of NAD+ added to the reagent. In the case of the GPT assay, therefore, it was found that the equilibrium equation works out to $$\frac{0.27 \text{ mM}}{6.1} = 45 \ \mu M \ NAD^+$$

Therefore, 50 μM of NAD+ can also be added to the stabilizer in order to maintain the concentration of NADH at a level of about 0.27 mM. Of course it is not necessary to add NAD+ if sufficient NADH is present to provide a source of NAD+, once oxidized, to set up the equilibrium. However, it is more expedient to add the requisite NAD+ at the outset in order to provide equilibrium conditions at the time the diagnostic reagent is prepared.

For illustrative purposes, the following describes suitable ranges for the components of the stabilizer when glucose dehydrogenase is the catalyst:

| COMPONENT | GENERIC RANGE | PREFERRED RANGE |
|---|---|---|
| 1) NAD+ | 0.1–2000 μM | 50–850 μM |
| 2) Glucose | 0.05–600 mM | 0.5–60 mM |
| 3) GDH | 0.01–50 U/L | 0.01–1 U/L |

An exemplary stabilizer of this invention containing glucose dehydrogenase (GDH) as the stabilizer enzyme uses glucose as the stabilizer substrate to perform the following reaction:

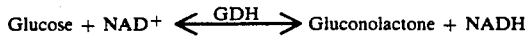

Glucose + NAD+ ⇌ GDH → Gluconolactone + NADH

The stabilizer, containing the GDH, glucose and a defined amount of NAD+, was added to a diagnostic reagent comprising degraded NADH and a phosphate buffered GPT reagent. The stabilizer of this invention was successful in at least doubling the stability of the GPT reagent. The unstabilized reagent has a stability of about 4 days at 2°–8° C., while the diagnostic reagent prepared with stabilizer containing the NADH regeneration reagents was stable for up to 21 days under similar conditions. Furthermore, the presence of the stabilizer did not affect the performance of the diagnostic reagent.

It is also possible for the stabilizer to not contain added NAD+, of course, by there being an adequate amount of NADH present in the diagnostic reagent to provide a source of sufficient NAD+ upon oxidation, so that the same equilibrium will be achieved as the amount of NAD+ increases. The purpose of adding NAD+ in the stabilizer, therefore, is merely to set up the equilibrium conditions at the beginning.

Suitable substrates for the stabilizer enzyme will vary depending upon the enzyme used, reaction conditions, etc. It is possible for the substrate to be either a substrate which is consumed during the reaction or a pseudosubstrate which triggers the enzyme to catalyze the NAD+ reduction without being consumed in the reaction. Suitable substrates or pseudosubstrates for the various enzymes suitable in the recovery reaction are well known to one of ordinary skill in the art, or are routinely determinable.

In addition to the stabilizer components noted above, it is also contemplated that the stabilizer may contain other additives which may affect the performance of the stabilizer, e.g., mutarotase may be added to increase the availability of the B-isomer of glucose in the GDH stabilizer, which in turn will increase the rate of reaction of GDH, thereby allowing the use of less GDH to perform the reaction at particular rate of reaction. These additives and other modifications can be adapted by one of ordinary skill in the art by routine experimentation to carry out this invention.

In addition to the enzymatic methods detailed above, it is also within the scope of this invention to regenerate NADH in a careful and controlled way by means of chemical and physical regeneration methods, so long as the criteria discussed above for controllability and predictable equilibrium are met. Thus, for example, chemical methods such as the phenazine methosulfate and 2,6-dichlorophenol-indolphenol methods can be used. See. e.g., Pinder, et al., Meth. Enzym., D. B. McCormick et al eds., Vol. XVIII, B, p. 20, New York, Academic Press (1971). In addition, other chemical catalytic methods can be routinely adapted by one of ordinary skill in the art by utilizing the principles developed for the control of the rate and equilibrium of the enzymatic reactions to modify the known chemical and physical methods.

This invention utilizes, in addition to the NADH stabilizer, a related approach to solve not only the inherent instability of the NADH in solution, but also the instability of the assay itself.

In addition to the above-mentioned problem of instability of NADH in the diagnostic reagent, the enzymatic assay for $CO_2$ has been plagued with additional problems caused by the instability of the calibration curve due to the absorption by these solutions of atmospheric $CO_2$. Within a very short period of time, e.g., generally 4–6 hours, the amount of $CO_2$ which is absorbed by the diagnostic solutions will change the reagent blank. Thus frequent calibration is necessary and reagent and time is wasted by recalibration. This causes great trouble and expense in the use of this enzymatic assay for the presence of $CO_2$, and there have been numerous, generally partially successful, efforts made to alleviate the problem. See, for example, the Boehringer Mannheim Diagnostics method, which includes reducing the pH of the reagent solutions and using a $CO_2$ scrubber.

The conventional enzymatic assay for $CO_2$ takes advantage of the following reaction scheme:

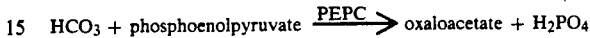

The enzymatic reagents are generally present as two components to allow sample blanking and minimize interference, wherein the enzymes required for the reaction are kept separate from the substrate and coenzyme, and the enzymes are added to the rest of the reactants to start the reaction; thus, component (i) comprises, e.g., NADH, substrate (phosphoenolpyruvate), and buffer, while component (ii) comprises the phosphoenolpyruvate carboxylase and the malate dehydrogenase, in a more concentrated form. Of course, the components can be comprised in other suitable arrangements such that no one component contains all of the reactants necessary to start the reaction.

In order to perform this two reagent $CO_2$ test, generally the sample is added to the NADH-buffer component, and the second component containing the remaining reagents necessary to complete the reaction is added. The absorbance at 380 nm is measured, to detect the oxidation of NADH (it is noted that measuring the absorbance of NADH at 380 nm, where NADH absorbs less strongly than at 340 nm, allows the use of higher concentrations of NADH than does detection at 340 nm). The difference in absorbance before the addition of the second component and after the addition is proportional to the total bicarbonate present in the reaction solution. This of course includes the presence of bicarbonate from the sample and bicarbonate formed from dissolved atmospheric $CO_2$. A blank for the presence of dissolved $CO_2$ in the diagnostic reagent consists of all of the reagents with no sample. The reading for the blank is then subtracted from the reading for each sample to give the true value for the bicarbonate concentration in the sample. In order to obtain valid results, it is imperative that the reading for the blank remain constant during the useful calibration period.

However, as noted above, the amount of dissolved $CO_2$ in the reaction solutions does not remain constant. Therefore, it has long been a goal to find a way to avoid this problem.

This goal has been achieved by adding a stabilizer utilizing the above-mentioned NADH recovery method to the reagents of component (i), and in addition, a $CO_2$-removing stabilizer. Preferably, the stabilizer comprises the enzymes of component (ii), wherein at least one of said enzymes is at rate-limiting concentrations, such that a substantially constant level of dissolved $CO_2$ is maintained in component (i). The amount of the rate-limiting reactant is preferably very carefully calculated, in order that it provide an adequate rate of removal of $CO_2$ from the diagnostic reagent during storage, yet not interfere in the far higher rate of reaction initiated upon addition of diagnostic levels of the reactants of component (ii) upon actual use of the reagent. However, due to the use of the NADH-recovery stabilizer, it is also possible to utilize a one-component reagent for enzymatic $CO_2$ detection, as the NADH which is being oxidized during the reaction which removes dissolved $CO_2$ from the solution is constantly recovered by the NADH-recovery stabilizer, and can be utilized to control the rate of reaction even in the presence of non-rate-limiting amounts of the diagnostic enzymes.

Thus, for example, it has been found that the addition of 2 U/L of malate dehydrogenase and 20 U/L of phosphoenol-pyruvate decarboxylase to component (i) is sufficient to increase the calibration stability of the $CO_2$ assay, using an Hitachi 737 analyzer, from less than 4 hours to 120 hours. For comparison, after addition of a component (ii) to component (i) under standard conditions of a conventional enzymatic $CO_2$ test (EM Diagnostics Systemate Bicarbonate assay), the final concentration of MDH in the diagnostic assay is 2136 U/L and the final concentration of PEPC is 370 U/L. Therefore, the addition of very small, rate-limiting amounts of the component (ii) of the assay is sufficient to control the accumulation of $CO_2$ which destabilizes the assay without interfering in the reliability of the assay itself.

It is notable that, for this particular assay, although either of the enzymes MDH or PEPC can be used as the rate-limiting component, MDH is the more stable of the two, and it is therefore preferred that the concentration of MDH be the rate-limiting component. However, it is also important to note that the concentration of PEPC is also to be kept to a minimum, although in theory any concentration of the non-rate-limiting enzyme can be used. This requirement is due to the fact that many preparations of PEPC are either contaminated by or manifest endogenous NADH oxidase activity, which adds to the problem caused by non-enzymatic losses of NADH during storage conditions.

Thus, as noted above, in addition to the stability of the assay related to the problem of absorbed $CO_2$, this assay is also plagued by the usual problems related to this $CO_2$ assay which utilizes NADH, and, furthermore, there is the problem caused by the endogenous PEPC-associated NADH oxidase activity, further adding to the NADH stability problem. And still further, under the conditions disclosed above, the $CO_2$ stabilization is performed at the expense of NADH present in the solution. Therefore, as in the other NADH-dependent assays discussed above, it is also necessary, and in fact even more important, to employ the NADH stabilizer of this invention in this $CO_2$ assay, in order to maintain constant levels of NADH lost both to the usual oxidation problems during storage, the endogenous NADH oxidase activity of the diagnostic enzymatic reagent, as well as to the $CO_2$ stabilization reaction, which oxidizes NADH to $NAD^+$ in the process of removing bicarbonate from the solution.

In order to determine appropriate amounts of the various enzymes and substrates for the stabilizer additives, the following considerations are taken into account. First, assume a low but normal bicarbonate concentration in a biological sample is about 25 mmol/L. Most testing protocols utilizing the above-described reactants and, usually, automated analyzers, will dilute this sample no more than 100 fold. Therefore, there will be about 250 $\mu$mol/L of bicarbonate in the test reagent.

By definition, 1 unit of enzyme converts 1 $\mu$mol/L/min of substrate to product; therefore, a rate-limiting 2 units of MDH or PEPC would produce no more than 2 $\mu$mol/L/min of $NAD^+$. Since most clinical diagnostic reaction schemes require 4 minutes of reaction time, a total of 8 $\mu$moles of $NAD^+$ would be produced by the contribution of the stabilizer during the reaction period for the diagnostic reaction. At 25 mmol/L of bicarbonate, this is about 3% interference.

It was found that the addition of similarly rate-limiting and equilibrium-maintaining amounts of the NADH stabilizer of this invention, e.g., 4 U/L of the NADH-regenerating enzyme glucose dehydrogenase and an excess of glucose substrate for the enzyme, was sufficient to compensate for both the non-enzymatic oxidation of NADH and the NADH oxidase activity of the PEPC, as well as the NADH oxidized during the stabilization of $CO_2$, without interfering with the detection of the diagnostic reaction, which occurs at a vastly higher rate. In fact, using as stabilizing additives 2 U/L MDH
20 U/L PEPC
500 mg/dL glucose
4 U/L GDH, the calibration stability of the Systemate (EM Diagnostics, Gibbstown, N.J.) $CO_2$ assay on the Hitachi 737 analyzer was increased from less that four hours to over 120 hours, and similar results were also observed on the Olympus AU 5000 analyzer. This represents a very significant achievement in the stability of the reagents for this assay.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, are hereby incorporated by reference.

EXAMPLES

Example 1: Stabilization of the GPT Diagnostic Reagent with Glucose Dehydrogenase A dry commercial phosphate buffer-based GPT reagent (EM Diagnostic Systems, N.J.), which is usually stable for 4 days at 2°-8° C. after reconstitution was reconstituted with water, or with the stabilizer diluent described below. The stability of the reconstituted solutions was then tested by measuring the absorbance at 340 nm, the reagent being considered fully functional as long as the absorbance is at least 1.2 absorbance units.

The reagents for the initial stabilizing solution were prepared as follows:

---

1. Glucose Dehydrogenase stock solution (1.0 U/mL)
   To 10 mL 0.1 M phosphate buffer, pH 7.4, add
   0.75 g NaCl and
   10 U glucose dehydrogenase (e.g., from Bacillus)
2. Diluent for GPT Test (stabilizing solution)
   To 150 mL deionized $H_2O$, add
   750 mg glucose -continued 10.0 mg NAD+ (= 100 μM)
150 μL glucose dehydrogenase stock solution (= 1 U/L)

Bottles of GPT reagent normally reconstituted with water were instead reconstituted with the diluent prepared above, and compared with the water-reconstituted reagent.

The change in absorbance of these reagents at 340 nm was monitored with a Gilford Response UV-VIS spectrophotometer. The results are described in Table 1.

TABLE 1

| TIME AFTER RECONSTITUTION | STORAGE TEMP (°C.) | ABSORBANCE AT 340 nm | |
|---|---|---|---|
| | | CONTROL REAGENT | STABILIZED REAGENT |
| 1. 0 HR | 25 | 1.734 | 1.761 |
| 2. 44 HR | 25 | 0.949 | 1.547 |
| 3. 68 HR | 25 | 0.647 | 1.178 |
| 1. 0 DAYS | 2–8 | 1.734 | 1.668 |
| 2. 3 DAYS | 2–8 | 1.416 | 2.027 |
| 3. 6 DAYS | 2–8 | 1.327 | 1.917 |
| 4. 10 DAYS | 2–8 | 1.175 | 1.726 |
| 5. 11 DAYS | 2–8 | 1.018 | 1.535 |
| 6. 16 DAYS | 2–8 | 0.903 | 1.418 |
| 7. 22 DAYS | 2–8 | 0.761 | 1.232 |

Thus it can clearly be seen that the stabilized reagent was fully functional for 22 days, a vast and dramatic improvement over the previous 4 days of stability of the unstabilized reagent.

Example 2: Determination of suitable concentrations for the stabilizing reagents in the GPT assay A. Preliminary experiments were performed to determine appropriate ranges for the stabilizing reagents. The concentrations were estimated as follows:

The concentrations of the components of a standard GPT diagnostic reagent was used, i.e.,

| R1: | L-alanine | 800 mM |
| | NADH | 0.27 mM |
| | Phosphate buffer (pH 7.4) | 80 mM |
| R2: | 2-oxoglutarate | 0.18 mM |

For the concentration of glucose, the substrate of the stabilizing enzyme glucose dehydrogenase, an amount was estimated which would be 100 times the concentration of NADH present in order to drive the reaction:

0.026 mM × 100 = 26 mM = 468 mg/dL glucose

A concentration of 500 mg/dL was used (=28 mM).

For the concentration of glucose dehydrogenase, suitable experimental amounts were estimated as follows:

In a standard GPT assay, 25 U/L is a normal sample concentration of glutamate-pyruvate transaminase. In order to achieve an NADH-recovery rate of about 2% interference, an amount of GDH was calculated which would approximate that rate:

25 U/L × 0.02 = 0.5 U/L GDH

Taking into account that the sample is diluted about 1:10 with reagent in the standard assay, the amount of GDH was further adjusted:

$$\frac{0.5\ U/L}{10} = 0.5\ U/L$$

This being a rough estimate, activities varying from 0.07 U/L to 40 U/L were chosen in order to determine experimentally an optimal amount of GDH for further testing.

The automated parameters used for the test on an EPOS batch analyzer were as follows:

| | |
|---|---|
| Reaction measurement time: | 60 sec. |
| Incubation time between addition of second reagent and beginning of measurement period: | 36 sec. |
| Preincubation time between addition of sample and addition of second reagent: | 84 sec. |
| No sample or reagent blanks | |
| A calibration factor of: | 1052 |
| Sample volume: | 46 μL |
| Reagent 1 volume: | 230 μL |
| Reagent 2 (2-oxoglutarate) volume: | 23 μL |
| Temperature: | 25° C. |
| Wavelength (closest available to 340 nm): | 344 nm |

The results of this experiment are shown on Table 2:

TABLE 2

| | NADH RECOVERY AT 340 NM AFTER 54 HR AT 25° C. | GPT CONTROL SERUM RECOVERY |
|---|---|---|
| Control (no GDH) | 42% | 100% |
| 0.07 U/L GDH | 47% | 100% |
| 0.3 U/L GDH | 55% | 100% |
| 40 U/L GDH | 56% | 85% |

CONCLUSIONS:
1. A desirable effect was observed at 0.3 U/L GDH, with no interference with the GPT assay.
2. At a concentration of 40 U/L, there was a >15% negative interference with the GPT assay. There-fore, this high a concentration of GDH is too high.
3. The regeneration method overall needed further optimization, as it was not very effective, although clearly better than without stabilization.

B. In order to further optimize the stabilization reaction conditions, the effects of the concentrations of NAD+ and NADH under the optimal equilibrium conditions were next taken into consideration.

The NADH stabilization system ultimately uses glucose as a reducing substance in the presence of GDH to recover NADH as it is oxidized to NAD+. The enzyme does not affect the equilibrium between NAD+ and NADH, but rather facilitates the rapid establishment of the equilibrium. Of course this means that immediately upon addition of GDH, there is a drop in the concentration of NADH, and a concomitant drop in the absorbance at 340 nm, as equilibrium amounts of NADH are converted to NAD+ and the equilibrium is established. Therefore, in order to optimize the equilibrium for NADH at a concentration which is optimal for the various diagnostic reactions, an amount of NAD+ was calculated which, when added with the other stabilizer reagents, would allow the immediate establishment of equilibrium conditions without lowering the amount of NADH added as a part of the standard diagnostic reagent. Standard routine experiments were performed to determine an appropriate concentration of NAD+ to add to the stabilized diagnostic assays. As shown in Table 2, it was found that adding 100 μM NAD+ was more than enough to prevent a drop in absorbance at 340 nm upon addition of the GDH. Using these concentrations, and the data obtained at equilibrium, it is possible to determine an appropriate concentration of NAD+ to use, e.g.:
Glucose concentration = 500 mg/dL (28 mM)
NADH concentration = 269 µM
NAD+ concentration = 100 µM
At equilibrium:
NADH found = 317 µM
NAD+ = 52 µM (100−(317−269))
NADH/NAD+ = 317/52 = 6.1

Therefore, the optimal ratio of NADH/NAD+ for establishing equilibrium conditions at a preset NADH concentration is about 6 to 1.

C. Using these figures, the reagent concentrations for the GPT assay were calculated and stability experiments performed on the resulting stabilized solution.

In the GPT assay which was tested, the starting concentration of NADH was 0.270 mM. Thus the calculation of the approximate amount of NAD+ needed to preform the equilibrium conditions is calculated as:

$$\frac{270 \; \mu M \; NADH}{6.0} = 45 \; \mu M \; NAD^+$$

The actual stabilizer additive concentrations tested were as follows:
GDH = 1 U/L
glucose = 28 mM (500 mg/dL)
NAD+ = 50 µM The results are shown in Table 3:

TABLE 3

| HRS. AFTER RECONSTI- TUTION | CONTROL STORAGE TEMP. (°C.) | STABILIZED REAGENT ABS. (% RECOVERY) | REAGENT ABS. (% RECOVERY) |
| --- | --- | --- | --- |
| 0 | 25 | 1.694 (100%) | 1.738 (100%) |
| 1 | 25 | 1.629 (96%) | 1.731 (100%) |
| 3 | 25 | 1.556 (92%) | 1.753 (101%) |
| 4 | 25 | 1.493 (88%) | 1.764 (101%) |
| 22 | 25 | 1.086 (64%) | 1.557 (90%) |
| 28 | 25 | 0.965 (57%) | 1.446 (83%) |
| 46 | 25 | 0.690 (41%) | 1.094 (63%) |
| 51 | 25 | 0.603 (36%) | 0.984 (57%) |

CONCLUSIONS
1. The amounts of NAD+, glucose and GDH chosen seems to be sufficient to double the stability of the NADH in the GPT reagent.
2. The criteria for selecting the concentrations of stabilizer components are:
1) Glucose = 100 × [NADH]
2) GDH = 2% of the normal rate of conversion of NADH → NAD+ in the reagent
3) [NAD+] = [NADH]/6

Example 3: Determination of the maximum limits on the rate of recovery of NADH using GDH as the stabilizer A. In order to determine the uppermost limits on the rate of recovery of NADH in a diagnostic assay, the amount of GDH added to a standard assay for lactate dehydrogenase was varied over a range of 0–100 U/L, using 128 U/L of lactate dehydrogenase as a standard. FIG. 1 shows the result of this test. It can be seen that at a level of about 20 U/L of GDH, which is about 16% of the concentration of LDH, the interference of the GDH in the apparent activity of the LDH is about 10%. This is probably higher than a diagnostically acceptable rate of interference. At a concentration of 0.4 U/L, the interference is almost not measurable.

Figure 2:
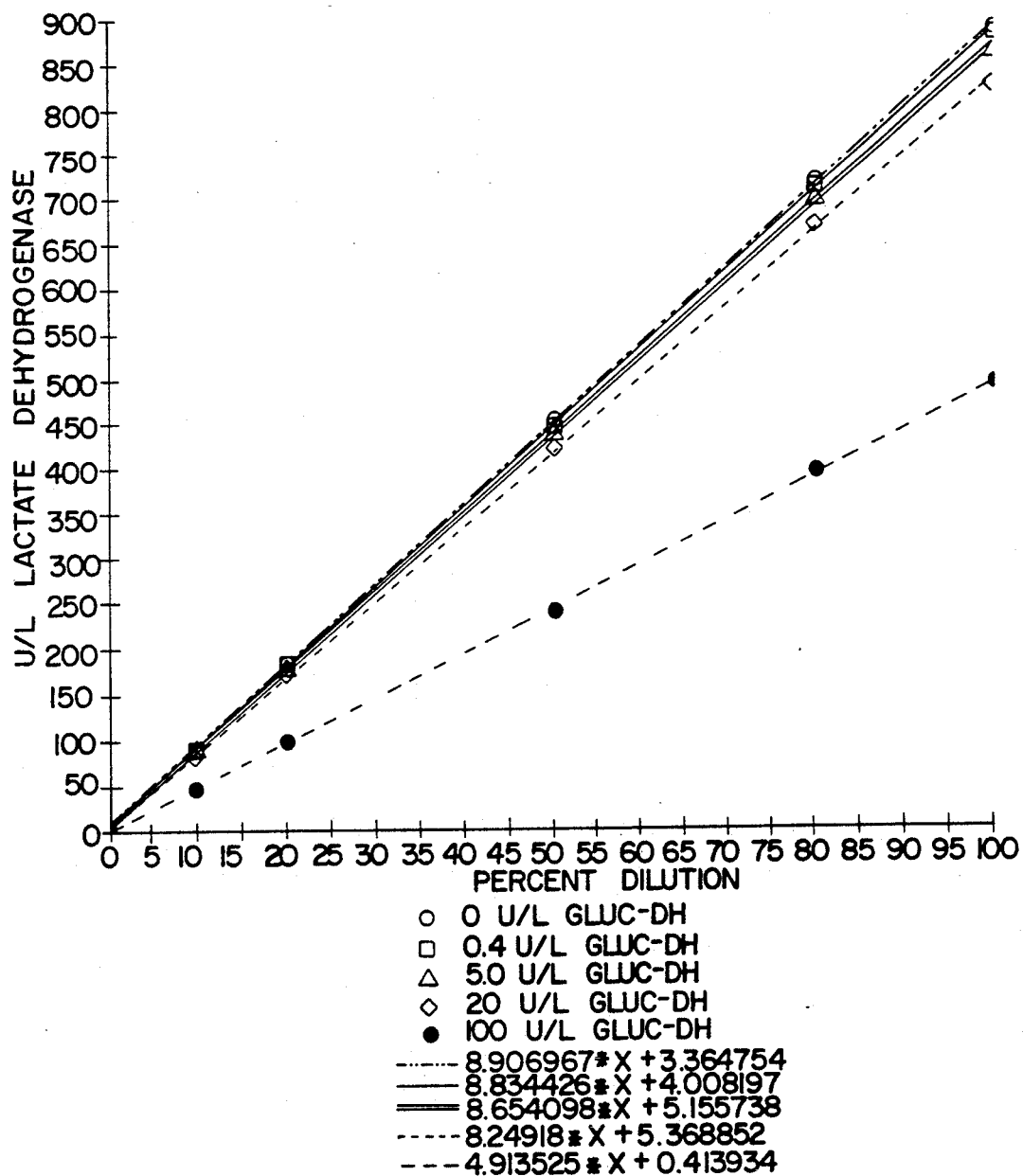
FIG. 2 shows the effect of various concentrations of GDH on the linearity of the assay for LDH.

B. A further test for the suitable limits of concentration for the stabilizer is to test the linearity of the resulting stabilized diagnostic assay. FIG. 2 shows the results of adding various amounts of GDH to an LDH diagnostic assay reagent. This shows a similar range of interference as is shown in FIG. 1 over the entire LDH range. At a level of 100 U/L of GDH, the LDH results are about half of the actual concentration, while up to 5 U/L shows little interference.

Example 4: Stabilized $CO_2$ Reagent

Using the NADH recovery system, and, in addition, a related method of removing $CO_2$ from diagnostic reagent solutions, a stabilized $CO_2$ reagent had also been developed.

A typical two part reagent for assaying the concentration of $CO_2$ at 380 nm generally includes:

| | |
| --- | --- |
| R1: NADH | 1.41 mmol/L |
| phosphoenol pyruvate | 5.63 mmol/L |
| sodium azide | <1 g/L |
| buffer | |
| R2: malate dehydrogenase (MDH) | 10,670 U/L |
| phosphoenolpyruvate carboxylase (PEPC) buffer | 1850 U/L |

The limits of usefulness of current reagent formulations include:

1. Limited Reconstituted Stability

Reconstitution of reagent is limited by atmospheric $CO_2$ absorption. The test system must have sufficient NADH capacity to react with bicarbonate absorbed from the atmosphere and bicarbonate from the test. As this bicarbonate blank increases there will eventually not be enough NADH to measure any additional bicarbonate from the sample.

2. Limited Calibration Stability

Current formulation continually absorb $CO_2$ from the air. This causes the blank to be continually increasing. The calibrated life of the reagent is determined by the rate of $CO_2$ absorption. Once this increase becomes sufficiently large, it will interfere with test results. This interference can be corrected by frequent blanking and calibration.

REASONING

Because the reagent formulations generally provide the majority of the liquid for the reaction to be present in R1, and R2 to be composed of concentrated enzymes, so that a small amount of R2 is added to a larger amount of R1 to start the reaction, the primary problem with $CO_2$ absorption occurs in R1. By adding an NADH stabilizer and by the addition of effective amounts of the diagnostic enzymes of R2 to the reagent mix of R1, dissolved $CO_2$ can be continuously removed from the reconstituted reagent solution. Thus, similarly to the general NADH stabilized diagnostic reagents discussed above, a stabilized $CO_2$ assay will have an NADH-recovery enzyme and substrate therefor, and, in addition, will contain effective amounts of all components of the $CO_2$-detection reaction. The diagnostic enzymes may be present in either diagnostically-effective amounts, in which case the assay may for the first time be present as a single-solution diagnostic reagent, or, preferably, smaller amounts of the diagnostic enzymes may be added to R1, in order to promote the removal of $CO_2$ while still allowing the diagnostic reaction to be started with precision upon addition of diagnostically-effective amounts of enzyme to a solution of R1 with sample already added.

DETERMINING THE CONCENTRATION OF STABILIZING REAGENTS

Assuming a low but normal bicarbonate concentration in a biological sample is about 25 mmol/L, and that most test protocols call for a 100-fold dilution of a sample in the reagent, there can be expected to be 250 μmol/L of $CO_2$ from the sample in the diagnostic reagent. By definition, 1 unit of enzyme converts 1 μmol/L/min of substrate to product. Since most test protocols require four minutes, at a concentration of 2 U/L of either MDH or PEPC, a total of 8 μmol of $NAD^+$ would be produced during the reaction period. At 250 μmol/L bicarbonate this would be about a 3% interference.

Of the two enzymes, MDH and PEPC, MDH is more stable and easily controlled. This enzyme therefore is best suited to be used as the rate-limiting enzyme to control the rate of removal of $CO_2$ from the reagent solution. PEPC can be used in any concentration; however, since PEPC usually contains some amount of NADH oxidase activity, it is important to keep this enzyme at a reasonably low concentration. 20 U/L PEPC was shown to be adequate.

However, it is further noted that, so long as the rate of NADH-recovery is limiting and adequate to keep the concentration of $CO_2$ constant and reasonably low, and the rate of NADH recovery correspondingly low, it is in fact possible for both of the diagnostic enzymes MDH and PEPC to be present in R1 in diagnostically effective amounts.

However, given the endogenous NADH oxidase activity of the PEPC, it is preferred that the $CO_2$-removing enzymes be present in limited amounts. Furthermore, if the enzyme concentration of the rate limiting $CO_2$-removing enzyme is the same as the concentration of the NADH-recovering enzyme (in terms of U/L), the rate of NADH oxidation by $CO_2$ removal and the rate of NADH reduction will just balance and the overall interference would be zero. Considering that there should be excess NADH reduction capability to account for endogenous NADH oxidase activity of the PEPC, and to account for NADH oxidation by dissolved oxygen, as discussed for the other NADH-requiring diagnostic reagents, a concentration of GDH of 4 U/L was selected.

Thus, the stabilizer reagents selected for R1 of the two-component $CO_2$ assay were as follows:
2 U/L MDH
20 U/L PEPC
500 mg/dL glucose
4 U/L GDH.

The results of the comparison of the stability of the stabilized $CO_2$ assay reagent with the unstabilized reagent is shown in FIG. 3. The comparison includes reagents stored both closed and open to the atmosphere.

CONCLUSION

Surprisingly, the calibration stability of the $CO_2$ assay was increased using the stabilizer of this invention from four hours to over 120 hours. Further routine optimization of the stabilization conditions and reagent concentrations should yield even better stabilities.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A method of stabilizing a diagnostic reagent for the detection of $CO_2$ in a solution containing said diagnostic reagent, which diagnostic reagent requires a coenzyme for activity, and wherein the reagent initially comprises at least two components,
   a first component (i) containing
      a first diagnostic substrate for a first diagnostic enzyme,
      a reduced form of the coenzyme, and
      optionally, a buffer, and
   a second component (ii) containing diagnostically effective amount of
      said first diagnostic enzyme and/or
      a second diagnostic enzyme;
   comprising adding to said first component a stabilizer, which comprises
      (a) a stabilizer enzyme which reduces the oxidized form of the coenzyme;
      (b) a substrate for the stabilizer enzyme; wherein the amount of (a) or (b) in the solution is rate-limiting and sufficiently low to reduce the oxidized coenzyme at a rate which is less than 10% of the lowest expected diagnostically significant rate of oxidation of the diagnostic reaction;
      (c) optionally, an amount of the oxidized form of the coenzyme sufficient to provide equilibrium conditions for the constant amount of reduced coenzyme and the amount of stabilizer enzyme present in the stabilized diagnostic reagent,
      (d) a rate-limiting and thereby $CO_2$-stabilizing amount of one of said first or second diagnostic enzymes, and
      (e) a non-rate-limiting amount of the other of said diagnostic enzymes,
   wherein the rate-limiting amount of (d) is sufficiently low to remove dissolved $CO_2$ from the solution at a rate which is less than 10% of the lowest expected diagnostically significant rate of removal of $CO_2$ of the diagnostic reaction.

2. A method of claim 1, wherein the amount of (a) or (b) is effective to achieve a substantially constant amount of reduced coenzyme in the solution under storage conditions.

3. A method of claim 1, wherein the component (a) is glucose dehydrogenase.

4. A method of claim 3, wherein the component (b) is glucose.

5. A method of claim 1, wherein said rate-limiting amount of one of the first or second diagnostic enzyme is effective to achieve a substantially constant amount of dissolved $CO_2$ in said first component (i) under storage conditions.

6. A method of claim 1, wherein the rate of reduction of oxidized coenzyme by the stabilizer enzyme is less than 5% of the lowest expected diagnostically significant rate of oxidation of the diagnostic reaction.

7. A stabilized diagnostic reagent for the detection of $CO_2$ in a solution containing said diagnostic reagent, which diagnostic reagent requires a coenzyme for activity, wherein the reagent initially comprises at least two components, a first component (i) containing
 a first diagnostic substrate for a first diagnostic enzyme,
 a reduced form of the coenzyme, and optionally, a buffer, and
a second component (ii) containing diagnostically effective amount of
 said first diagnostic enzyme and/or
 a second diagnostic enzyme;
comprising, included in said first component (i), a stabilizer, which comprises:
 (a) a stabilizer enzyme which reduces the oxidized form of the coenzyme;
 (b) a substrate for the stabilizer enzyme; wherein the amount of (a) or (b) in the solution is rate-limiting and sufficiently low to reduce the oxidized coenzyme at a rate which is less than 10% of the lowest expected diagnostically significant rate of oxidation of the diagnostic reaction;
 (c) optionally, an amount of the oxidized form of the coenzyme sufficient to provide equilibrium conditions for the constant amount of reduced coenzyme and the amount of stabilizer enzyme present in the stabilized diagnostic reagent,
 (d) a rate-limiting and thereby $CO_2$-stabilizing amount of one of said first or second diagnostic enzymes, and
 (e) a non-rate-limiting amount of the other of said diagnostic enzymes,
wherein the rate-limiting amount of (d) is sufficiently low to remove dissolved $CO_2$ from the solution at a rate which is less than 10% of the lowest expected diagnostically significant rate of removal of $CO_2$ of the diagnostic reaction.

8. A reagent of claim 7, wherein the oxidized coenzyme (c) is present.

9. A kit containing the reagents of claim 7 in separate and discrete containers, wherein component (i) contains a diagnostically effective amount of one of said diagnostic enzymes and component (ii) contains a diagnostically effective amount of the other diagnostic enzyme.

10. A kit of claim 9, wherein the diagnostic enzyme present in a diagnostically effective amount in component (i) is malate dehydrogenase and the diagnostic enzyme in component (ii) is phosphoenolpyruvate carboxylase.

11. A kit containing the reagents of claim 7 in separate and discrete containers, wherein component (ii) contains a diagnostically effective amount of both diagnostic enzymes.

12. A reagent of claim 7, wherein the amount of (c) or (d) in the solution is effective to achieve a substantially constant level of oxidized or reduced coenzyme in the solution under storage conditions.

13. A reagent of claim 7, wherein the amount of (a) is rate-limiting.

14. A reagent of claim 13, wherein
 (a) is glucose dehydrogenase;
 (b) is glucose, and
 (c) is $NAD^+$.

15. A reagent of claim 1, wherein the rate of reduction of oxidized coenzyme by the stabilizer enzyme is less than 5% of the lowest expected diagnostically significant rate of oxidation of the diagnostic reaction.

16. A reagent of claim 7, wherein
 (d) is malate dehydrogenase and
 (e) is phosphoenolpyruvate carboxylase.

17. A reagent of claim 7, wherein said rate-limiting amount of one of the first or second diagnostic enzymes is effective to achieve a substantially constant amount of dissolved $CO_2$ in said first component (i) under storage conditions.

18. In an enzymatic coenzyme-requiring diagnostic reagent for the detection of $CO_2$,
wherein
the reagent initially comprises at least two components, a first component (i) containing
 a first diagnostic substrate for a first diagnostic enzyme,
 a reduced form of the coenzyme, and
 optionally, a buffer, and
a second component (ii) containing diagnostically effective amounts of
 said first diagnostic enzyme and/or
 a second diagnostic enzyme;
the improvement wherein the reagent further includes, in said component (i), a stabilizer for minimizing accumulation of dissolved atmospheric $CO_2$ in the reagent solution and for minimizing loss of coenzyme in the reagent solution, which stabilizer comprises:
 (a) a stabilizer enzyme which reduces the oxidized form of the coenzyme;
 (b) a substrate for the stabilizer enzyme;
wherein the amount of (a) or (b) in the solution is rate-limiting and sufficiently low to reduce the oxidized coenzyme at a rate which is less than 10% of the lowest expected diagnostically significant rate of oxidation of the diagnostic reaction;
 (c) optionally, an amount of the oxidized form of the coenzyme sufficient to provide equilibrium conditions for the constant amount of reduced coenzyme and the amount of stabilizer enzyme present in the stabilized diagnostic reagent,
 (d) a rate-limiting and thereby $CO_2$-stabilizing amount of one of said first or second diagnostic enzymes, and
 (e) a non-rate-limiting amount of the other of said diagnostic enzymes,
wherein the rate-limiting amount of (d) is sufficiently low to remove dissolved $CO_2$ from the solution at a rate which is less than 10% of the lowest expected diagnostically significant rate of removal of $CO_2$ of the diagnostic reaction.

* * * * *